US007431713B2

(12) United States Patent
Harris et al.

(10) Patent No.: US 7,431,713 B2
(45) Date of Patent: Oct. 7, 2008

(54) INFUSION DEVICE WITH SAFETY GUARD

(75) Inventors: R. Bradley Harris, Ormond Beach, FL (US); Bret Reid, Ormond Beach, FL (US)

(73) Assignee: Command Medical Products, Inc., Ormand Beach, FL (US)

( * ) Notice: Subject to any disclaimer, the term of this patent is extended or adjusted under 35 U.S.C. 154(b) by 337 days.

(21) Appl. No.: 10/463,444

(22) Filed: Jun. 18, 2003

(65) Prior Publication Data

US 2004/0260250 A1 Dec. 23, 2004

(51) Int. Cl.
A61M 5/00 (2006.01)
A61M 5/32 (2006.01)
(52) U.S. Cl. ..................... 604/263; 604/198
(58) Field of Classification Search ............ 604/263, 604/192–198, 180, 164.08, 110, 117, 264, 604/163
See application file for complete search history.

(56) References Cited

U.S. PATENT DOCUMENTS

| 2,854,976 | A | 10/1958 | Heydrich |
|---|---|---|---|
| 3,324,853 | A | 6/1967 | Czorny et al. |
| 3,658,061 | A | 4/1972 | Hall |
| 3,822,701 | A | 7/1974 | Cloyd |
| 3,900,026 | A | 8/1975 | Wagner |
| 3,901,226 | A | 8/1975 | Scardenzan |
| 4,007,740 | A | 2/1977 | Owen |
| 4,129,128 | A | 12/1978 | McFarlane |
| 4,139,010 | A | 2/1979 | Dykstra |
| 4,250,880 | A | 2/1981 | Gordon |
| 4,500,312 | A | 2/1985 | McFarlane |
| 4,581,020 | A | 4/1986 | Mittleman |
| 4,627,843 | A | 12/1986 | Raines |
| 4,631,058 | A | 12/1986 | Raines |
| 4,804,371 | A | 2/1989 | Vaillancourt |
| 4,867,746 | A | 9/1989 | Dufresne |
| 4,883,469 | A | 11/1989 | Glazier |
| 4,886,503 | A | 12/1989 | Miller |
| 4,900,309 | A | 2/1990 | Netherton et al. |
| 4,982,842 | A | 1/1991 | Hollister |

(Continued)

OTHER PUBLICATIONS

"Finding Real Solutions: Blood Collection and Blood Culture," BD Safety Products Ordering Information, BD, Franklin Lakes, NJ (2001).

(Continued)

*Primary Examiner*—Matthew F Desanto
(74) *Attorney, Agent, or Firm*—Nixon & Vanderhye, PC (57) ABSTRACT

An infusion device has a body, flexible wings and a needle projecting generally at right angles from one end of the body. A guard is pivoted to the one end of the body. On one side, the guard has a channel so that the guard overlies the body in a first position thereof during application of the needle to the patient. The guard is pivotable through about 180° to a position generally parallel to the body and on a side of the needle remote from the body. As the needle is withdrawn from the patient, the guard is pivoted about 90° further to receive the needle between one or more flexible contoured members along the opposite side of the guard. The needle is thus captured and encapsulated within the guard, with audible confirmation, the members precluding the guard from pivoting away from the needle.

22 Claims, 9 Drawing Sheets

U.S. PATENT DOCUMENTS

| | | |
|---|---|---|
| 5,055,102 A | 10/1991 | Sitnik |
| 5,151,089 A | 9/1992 | Kirk, III et al. |
| 5,154,285 A | 10/1992 | Hollister |
| 5,188,611 A | 2/1993 | Orgain |
| 5,207,653 A | 5/1993 | Janjua et al. |
| 5,232,454 A | 8/1993 | Hollister |
| 5,232,455 A | 8/1993 | Hollister |
| 5,242,417 A | 9/1993 | Paudler |
| 5,312,369 A | 5/1994 | Arcusin et al. |
| 5,460,612 A | 10/1995 | Madore |
| 5,490,841 A | 2/1996 | Landis |
| 5,509,907 A | 4/1996 | Bevilacqua |
| 5,571,092 A | 11/1996 | Thompson |
| 5,669,889 A | 9/1997 | Gyure et al. |
| 5,681,295 A | 10/1997 | Gyure et al. |
| 5,709,660 A | 1/1998 | Doyle et al. |
| 5,755,695 A | 5/1998 | Erickson et al. |
| 5,921,969 A | 7/1999 | Vallelunga et al. |
| 5,931,815 A | 8/1999 | Liu |
| 6,261,259 B1 | 7/2001 | Bell |
| 6,328,713 B1 | 12/2001 | Hollister |
| 6,443,929 B1 | 9/2002 | Kuracina et al. |
| 6,676,633 B2 * | 1/2004 | Smith et al. ............ 604/110 |
| 6,824,530 B2 * | 11/2004 | Wagner et al. ............ 604/162 |
| 2004/0087912 A1 * | 5/2004 | Swenson ............ 604/263 |

OTHER PUBLICATIONS

"SurGuard2™ Syringe with Safety Needle (latex free)," http://www.terumomedical.com/SubDepts.asp, Copyright 2002, Terumo Medical Corp., dated Oct. 21, 2005.

"SurGuard2™ Safety Needles (latex free)," http://www.terumomedical.com/SubDepts.asp, Copyright 2002, Terumo Medical Corp., dated Oct. 21, 2005.

Surshield™ Safety Winged Blood Collection Set, http://www.terumomedical.com/blood_collection_desc.asp, Copyright 2002, Terumo Medical Corp., dated Oct. 21, 2005.

"BRICO Medical Supplies: Quality Supplies for Less," http://bricomedicalsupplies.com/tersafetysharps.html, Oct. 21, 2005.

"Safety Devices: Product News: Portex® Arterial Blood Sampling Kits with Low Heparin Formulation are Now Available," http://www.smiths-medical.com/therapy, Smiths Medical, Dec. 16, 2003, Copyright 2005, Smiths Groups plc, dated Oct. 21, 2005.

"The Next Generation of Safety is in Sight: LifeGuard™ Vision Safety Infusion Set," http://www.hmpvascular.com/needles, RITA Medical Systems, dated Oct. 21, 2005, pp. 1-3.

* cited by examiner

INFUSION DEVICE WITH SAFETY GUARD

BACKGROUND OF THE INVENTION

The present invention relates to an infusion device having a winged body with a needle projecting from the body generally at right angles in combination with a safety guard for capturing or encapsulating the needle after use to prevent needlestick injuries.

Needlestick injuries have been a common and recurring source of concern among medical practitioners because of the danger of transmission of various viruses, including HIV and Hepatitis B. Injuries to medical practitioners typically occur after the medication has been injected into the patient and before the needle has been rendered safe or placed in a sharps container. Many and various devices have been proposed and constructed in the past for protecting medical practitioners from needlestick injuries. Most such protective devices have been proposed and constructed for use with a conventional syringe where the needle projects axially from an end of the syringe barrel. For example, various types of sheaths have been proposed for capturing the needle or at least sheathing the tip of the needle after use. Other alternatives in conjunction with syringes of this type have provided various mechanisms for withdrawing the needle into the syringe barrel after use, thus using the barrel as the protective sheath to prevent the needlestick injury. However, while substantial effort has been made to protect against needlestick injuries when using conventional syringes, commensurate effort has not been made to protect against needlestick injuries when using an angled-needle infusion device.

An angled-needle infusion device generally includes a body having flexible wings projecting laterally from the body with a needle projecting generally at right angles to the body and the wings. The needle lies in communication with a fluid line carried by the body, and is typically coupled to an intravenous set. Conventionally, there is muscular tissue or a receiving port embedded under the patient's skin having a septum for receiving the needle. By grasping the wings of the angled-needle infusion device and flexing them upwardly, the needle can be directed into the septum or subcutaneous tissue and secured in place, for example, by taping the device to the patient's skin. Once infusion is complete, and the tape removed, the wings are again grasped and the needle is withdrawn. It is at this stage that the contaminated needle is exposed and the possibility of a needlestick injury is extant.

As noted previously, the effort to avoid needlestick injuries has been very broadly and primarily directed to preventing such injuries when using conventional syringes and comparable effort has not been directed to preventing such injuries when using an angled-needle infusion device. One such effort to safeguard an angled-needle infusion device has included a removable guard such as described and illustrated in U.S. Pat. No. 4,627,843, issued Dec. 9, 1986. Essentially, this requires applying the cap to the needle body to encase the needle. However, the needle and guard require manipulation by two hands and, hence, does not eliminate the danger of a needlestick injury when applying the guard to the needle. A further example of this type of guard is described and illustrated in U.S. Pat. No. 4,631,058, which suffers from the same deficiency. Accordingly, there is a need for a guard for an angled-needle infusion device which will substantially minimize or eliminate the danger of a needlestick injury during use.

BRIEF DESCRIPTION OF THE INVENTION

In accordance with a preferred embodiment of the present invention, there is provided an angled-needle infusion device having an elongated body and a pair of flexible wings straddling the body, together with a needle extending generally at right angles to the body adjacent one end thereof, in combination with a pivoted elongated needle guard. It will be appreciated that the body, wings and needle are of a conventional angled-needle infusion device construction with the needle in communication with a fluid line passing through the body of the device. The elongated guard is pivotally secured at one end, i.e., its proximal end, to the end of the needle body adjacent the needle. Particularly, the guard is pivoted to the body for movement between a first position overlying the needle body, through a range of about 270°, to a position capturing or encapsulating the needle. On one side of the guard, there is provided a channel such that the guard may overlie the body when the angled-needle infusion device is applied to the patient and the needle is inserted into the septum. The opposite side of the elongated guard includes a receptacle bounded by at least one and preferably two flexible members defining a tapered elongated slot. As the needle is withdrawn, the guard is pivoted into the second-position to capture or encapsulate the needle within the guard. The resilient nature of the flexible members precludes movement of the guard from the second position toward the first position whereby the needle is fully encapsulated by the guard, protecting against needlestick injuries.

More particularly, the guard has a pair of ears at its proximal end which straddle the distal end of the body adjacent the needle. The ears have a pair of slots which receive lateral projections on the end of the body. When the guard lies in the first position, the projections lie at one end of the slots. Upon movement of the guard into the second position, i.e., through about 270°, the guard slides relative to the projections to locate the projections in the opposite ends of the slots. This combination of pivoting and sliding movement orients the guard into a more parallel relation to the needle as the needle approaches the second position, facilitating entry of the needle into the guard. This slot design permits a needle position at the end of the winged body, along the user's line of sight, keeping the needle optimally visible for accurate positioning and insertion into patient.

To use the device, the guard overlies the body. Upon removal of a safety sheath from the needle, the angled-needle infusion device is applied in a conventional manner by grasping and flexing the wings and inserting the needle. When the needle is fully seated, the guard is rotated approximately 180° to lie generally parallel with the body and on the opposite side of the needle from the body. The angled-needle infusion device is then secured in place, e.g., by taping it to the patient's skin. Upon completion of the infusion, and after the tape is removed, the wings are again grasped, flexed and used to withdraw the needle. As the needle is withdrawn, the guard is rotated toward the second position, e.g., through a remaining arc of about 90°, such that the needle enters through the slot of the guard and is encapsulated. It will be appreciated that the movement of the guard into the second position, encapsulating and safeguarding the needle, is performed with one hand, i.e., the same hand which is removing the needle from the septum or tissue. Consequently, the danger of a needlestick injury by bringing another hand into contact with the needle is avoided.

In a preferred embodiment according to the present invention, there is provided an infusion device comprising an elongated body having a needle projecting from adjacent one end of the body and extending generally perpendicular to the body for transmitting fluid passing through the body into an injection site, a pair of flexible wings extending laterally from respective opposite sides of the body and lying generally in a plane perpendicular to the needle and an elongated needle guard having a receptacle extending along one side thereof and coupled to the body adjacent one end for pivotal movement through about 270° between a first position overlying the body and a second position receiving the needle within the receptacle.

In a further preferred embodiment according to the present invention, there is provided an infusion device comprising an elongated body having a needle projecting from adjacent one end of the body and extending generally perpendicular to the body for transmitting fluid passing through the body into an injection site, a pair of flexible wings extending laterally from respective opposite sides of the body and lying generally in a plane perpendicular to the needle and an elongated needle guard having a receptacle extending along one side thereof and coupled to the body, the guard being movable between a first position overlying the body in generally parallel relation thereto and a second position receiving the needle within the receptacle, the guard in the second position extending generally perpendicular to the body and generally parallel to the needle In a further preferred embodiment according to the present invention, there is provided a method of using and safeguarding an infusion device having an elongated body with flexible wings, a needle extending generally at right angles thereto and a guard pivotally, carried by the body adjacent one end thereof comprising the steps of (a) grasping the wings and inserting the needle into an injection site while the guard lies in a first position overlying the elongated body, (b) locating the guard in a position extended from the body and on a side of the needle remote from the body and (c) upon completion of the infusion, grasping the wings and rotating the guard into a second position to encapsulate the needle.

DETAILED DESCRIPTION OF THE INVENTION

Figure 1:
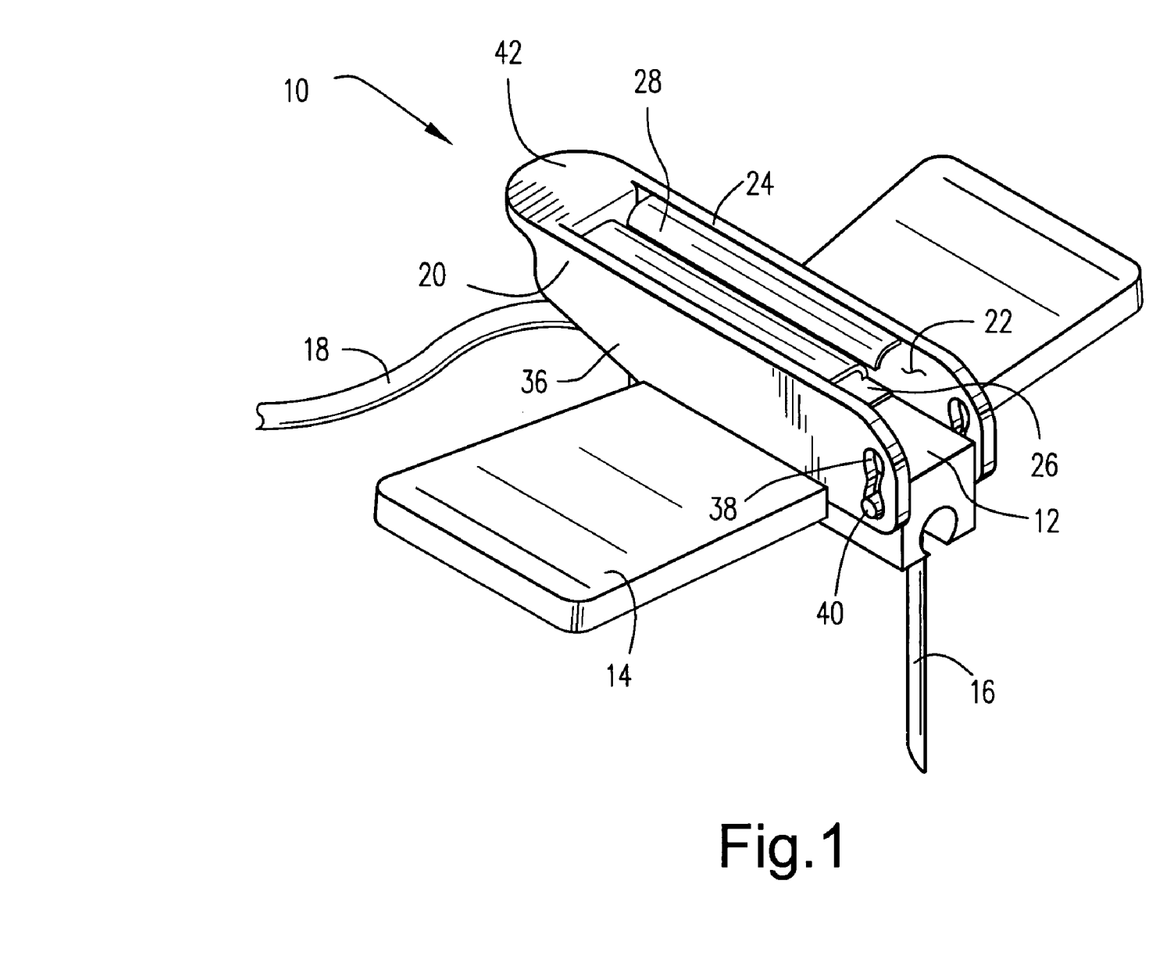
FIG. 1 is a perspective view of an infusion device according to a preferred embodiment of the present invention including a needle guard overlying the body of the device.
Figure 2:
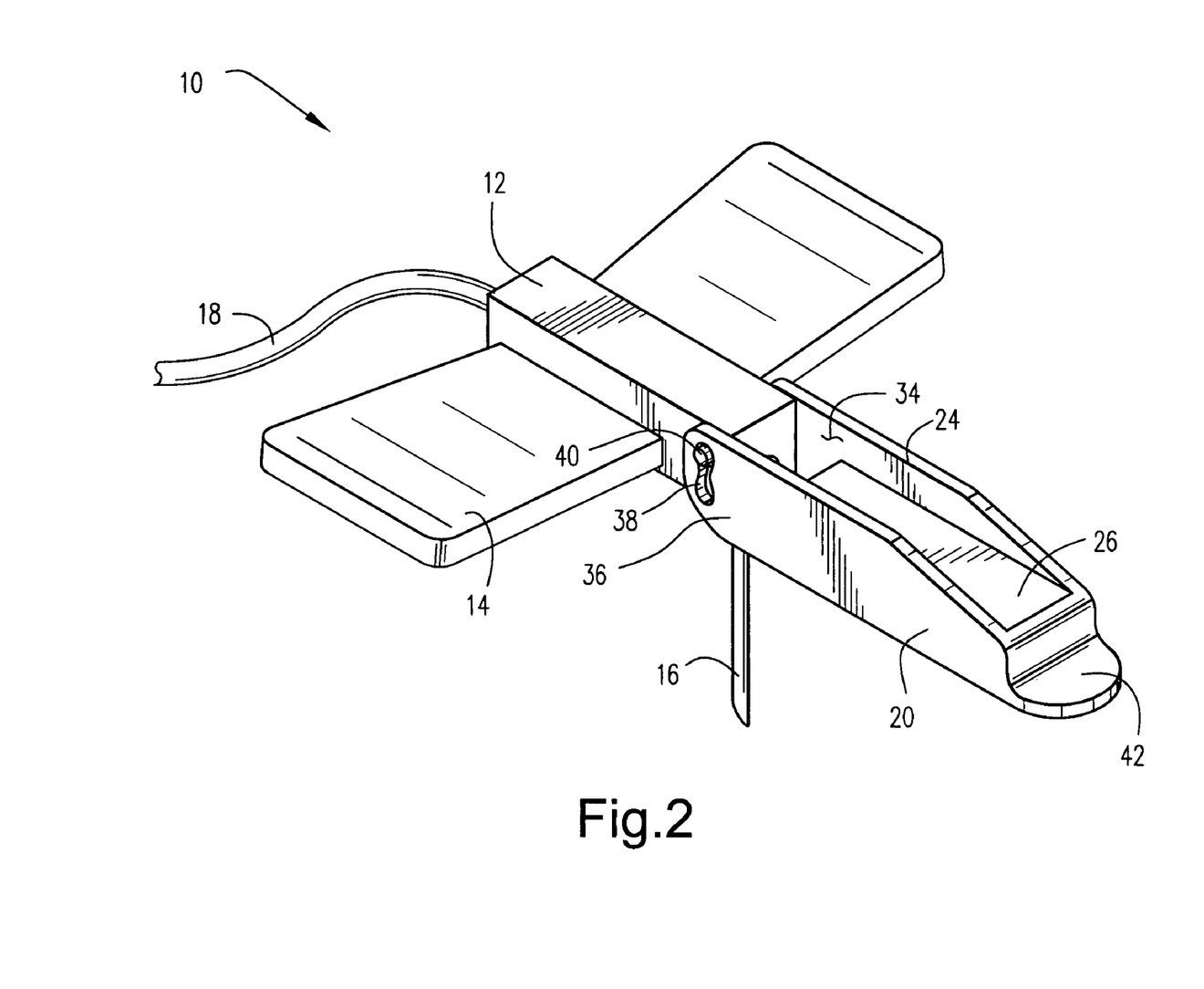
FIG. 2 is a view similar to FIG. 1, with the guard extended approximately 180°.

Referring now to the drawings, particularly to FIGS. 1 and 2, an infusion device according to a preferred embodiment of the present invention is generally designated 10 and includes an elongated body 12 carrying a pair of flexible wings 14 along opposite sides of the body 12 and a needle 16 projecting from one end of the body and generally at right angles thereto. The wings and body are preferably formed of plastic materials. It will be appreciated that the needle 16 lies in communication with an infusion line 18 for infusing medication into a port or subcutaneous tissue. The flexible wings 14 are used to grasp and manipulate the device for inserting the needle 16 into and removing the needle from subcutaneous tissue or the port.

Figure 3:
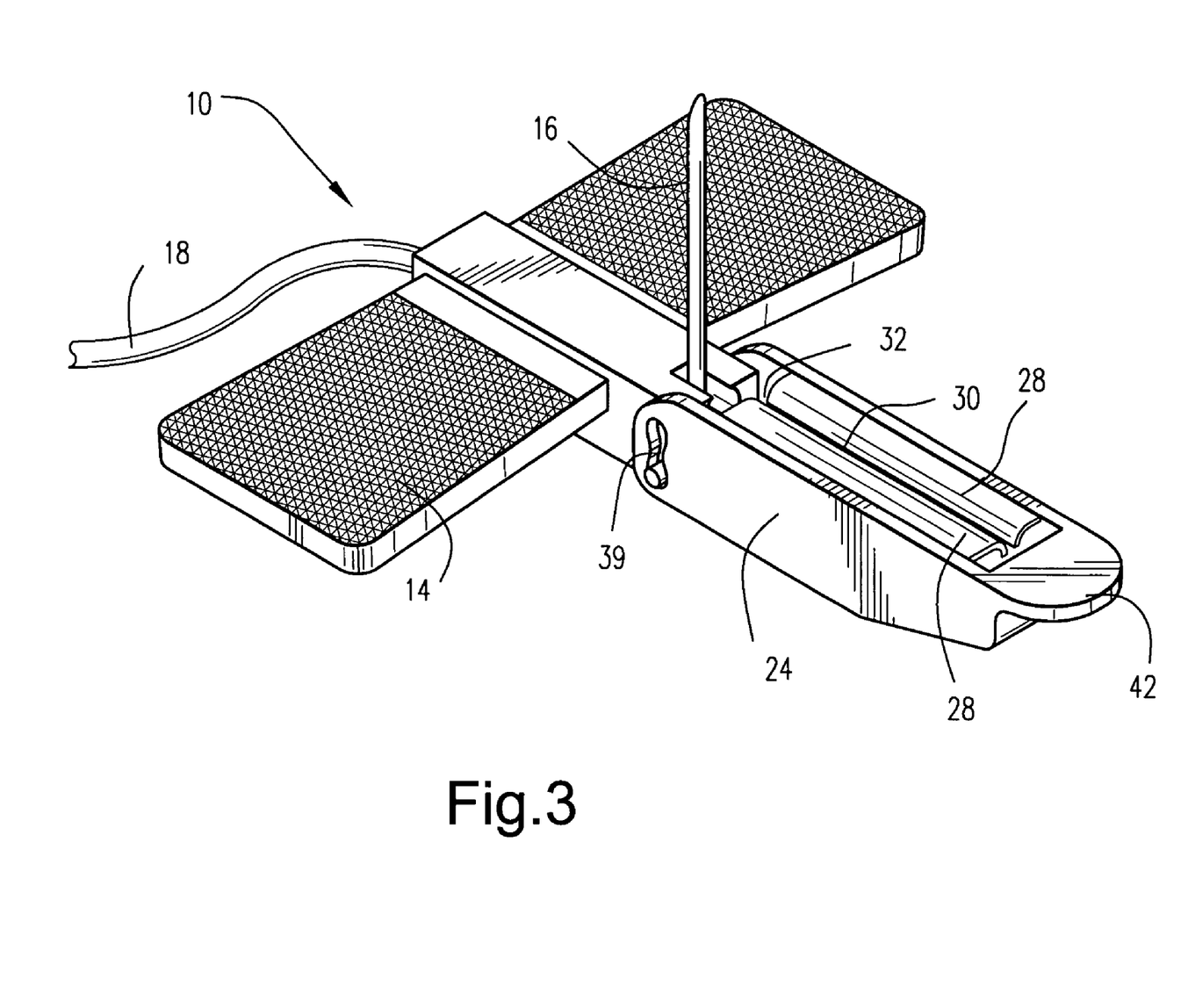
FIG. 3 is a perspective view illustrating the underside of the infusion device with the guard extended as in FIG. 2.
Figure 4:
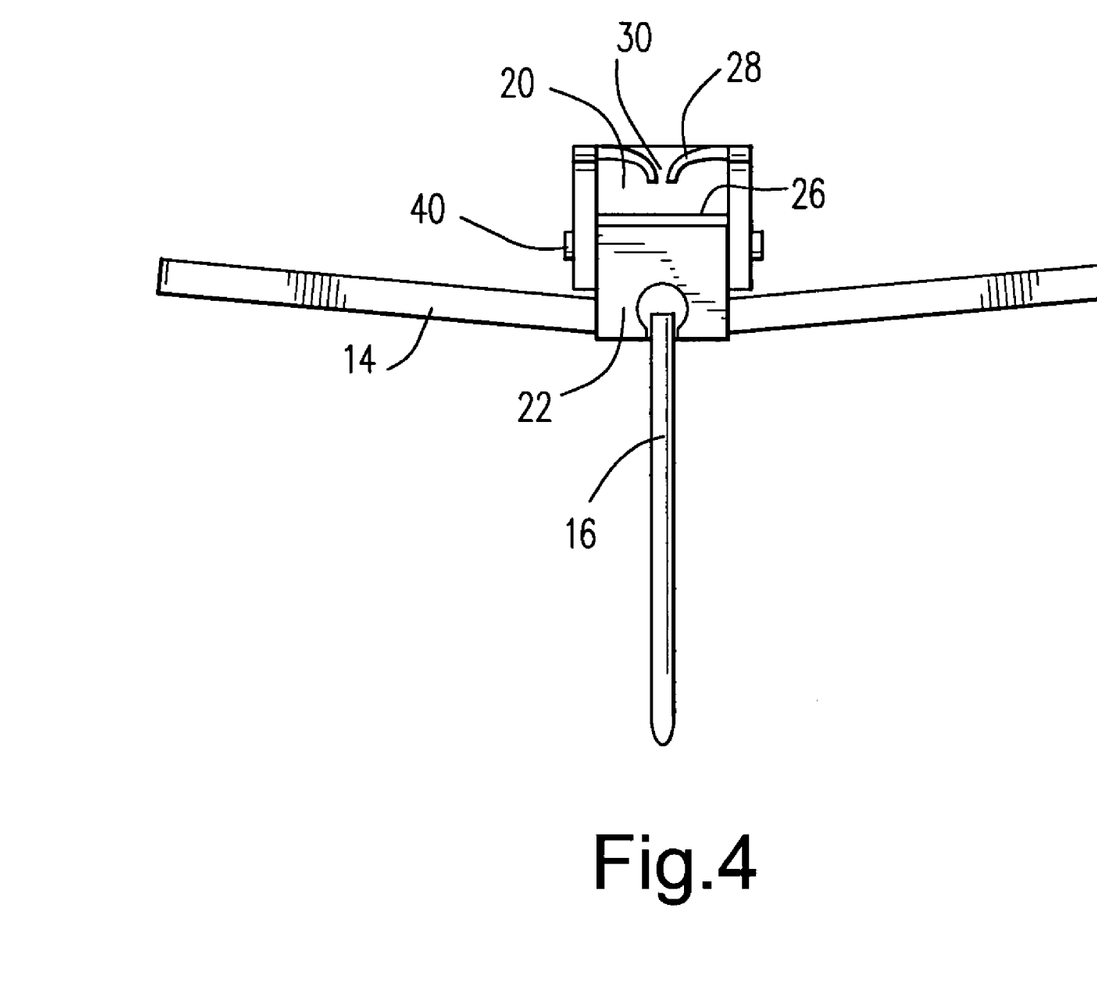
FIG. 4 is an end view of the infusion device of FIG. 1.
Figure 9:
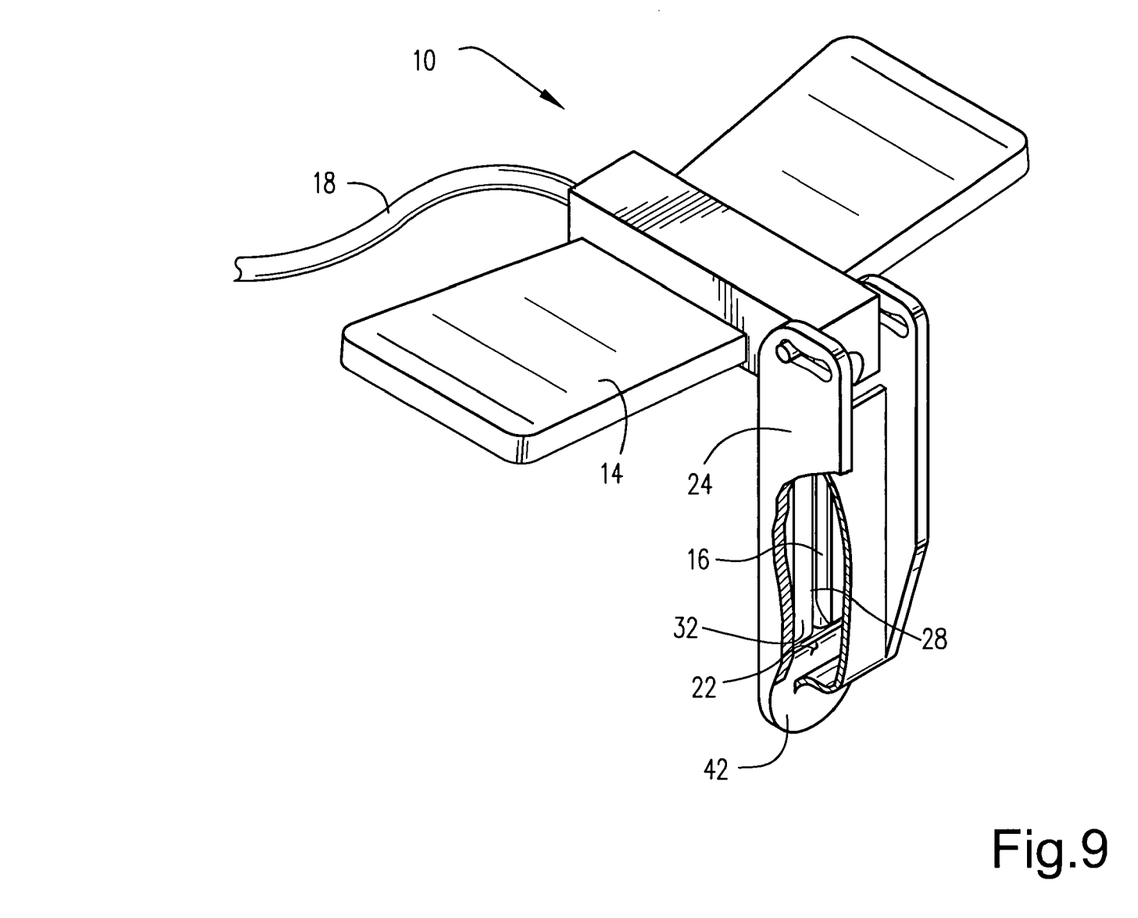
FIG. 9 is a perspective view of the infusion device with the needle encapsulated within the guard.

A guard 20 for the needle 16 and is pivotally secured to and adjacent one end, i.e., a distal end, of the body 12. The guard 20 is elongated and includes, as illustrated in FIGS. 1, 3 and 9, a receptacle 22 defined by the side walls 24 of the guard, an intermediate wall 26 extending lengthwise of the guard between the side walls 24 and at least one, and preferably a pair, of members 28 defining a slot 30 therebetween. The one or more members 28 are contoured to facilitate entry of the needle into the receptacle 22. More specifically, members 28 are tapered inwardly to define a tapered entry 32 through the slot 30 and into receptacle 22. The one or more members 28 are resilient and, hence, flexible, enabling the guard to receive the needle 16 into the receptacle 22 by flexing the one or more members inwardly. Upon deflection of the members and reception of needle 16 within the receptacle 22, the members return to their normal position, maintaining the needle within the receptacle 22.

On the opposite side of the guard 20 from the ribs 28 is a channel 34 defined between the side walls 24 and the intermediate wall 26. The channel receives the body 12 when the guard overlies the body 12 in a first position as illustrated in FIG. 1. The channel 34 provides the guard and body with a low profile similar to a conventional angled-needle infusion device without the guard. The guard 20 includes a pair of ears 36 at its proximal end which straddle the distal end of the body 12. The ears 36 have slots 38 for receiving projections or pins 40 carried by the distal end of body 12. Each of the slots 38 has a substantially medially located boss 39, preferably two opposed bosses 39 defining a restricted portion of the slot 38. Thus, the guard 20 is pivotally mounted on body 12 for movement from a first position overlying body 12 through a range of 2700 to a second position encapsulating the needle within the receptacle 22 of the guard. From a review of FIG. 3, it will be appreciated that the entry 32 to the slot 30 is spaced back from the proximal end of the guard and from the distal end of body 12 to facilitate the full range of pivotal movement and entry of the needle into the receptacle. The guard 20 also includes a tip 42 at its distal end to facilitate pivotal movement of the guard.

Figure 5:
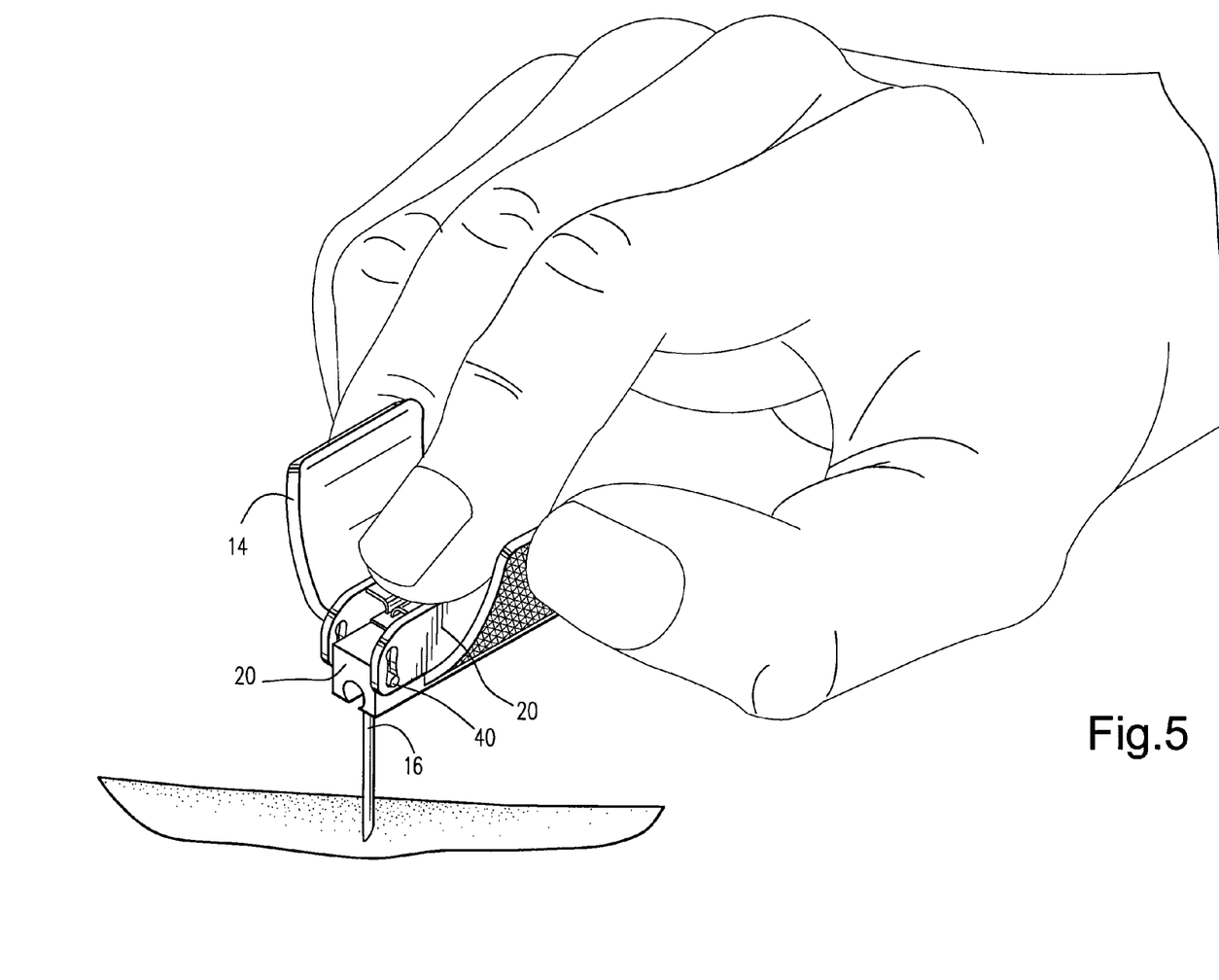
FIGS. 5, 6, 7 and 8 are sequential views illustrating the manner of use of the infusion device hereof.
Figure 6:
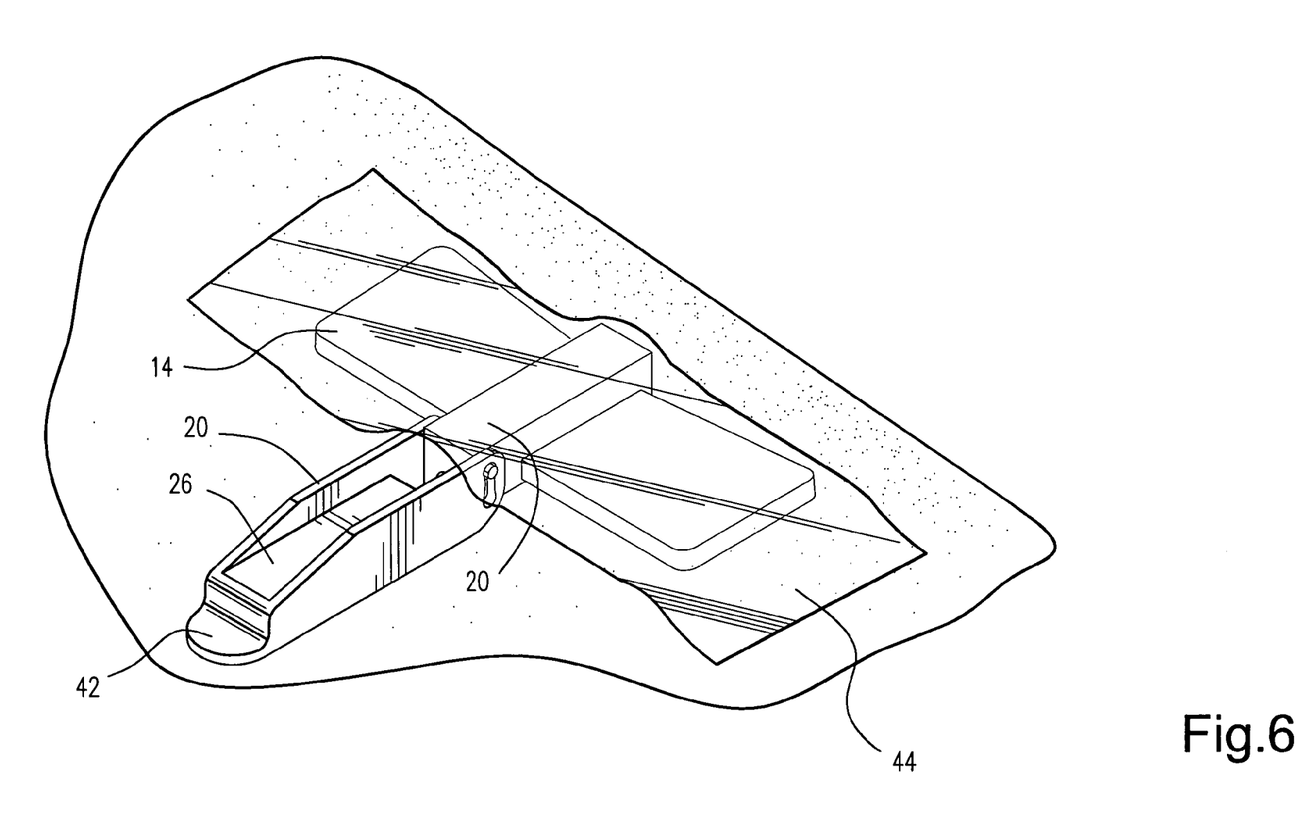

To use the infusion device hereof and referring to FIGS. 5-8, the guard 20 is initially provided in or pivoted into its first position overlying the body 12 as illustrated in FIG. 1. It will be appreciated that the channel 34 on one side of the guard 20 receives the upper portion of the body 12 in this first position of the device. The practitioner then grasps and flexes the wings 14, preferably with an index finger overlying the guard, in order to locate the needle over the injection site as illustrated in FIG. 5. The needle is then inserted beneath the skin and, as illustrated in FIG. 6, the wings return to their normal unflexed position. Additionally, the guard is rotated about the projections 40 approximately 180° to extend from the body 12 such that the guard lies on the side of the needle remote from body 12. The device is then secured to the injection site, for example, by using tape 44 (FIG. 6).

Figure 7:
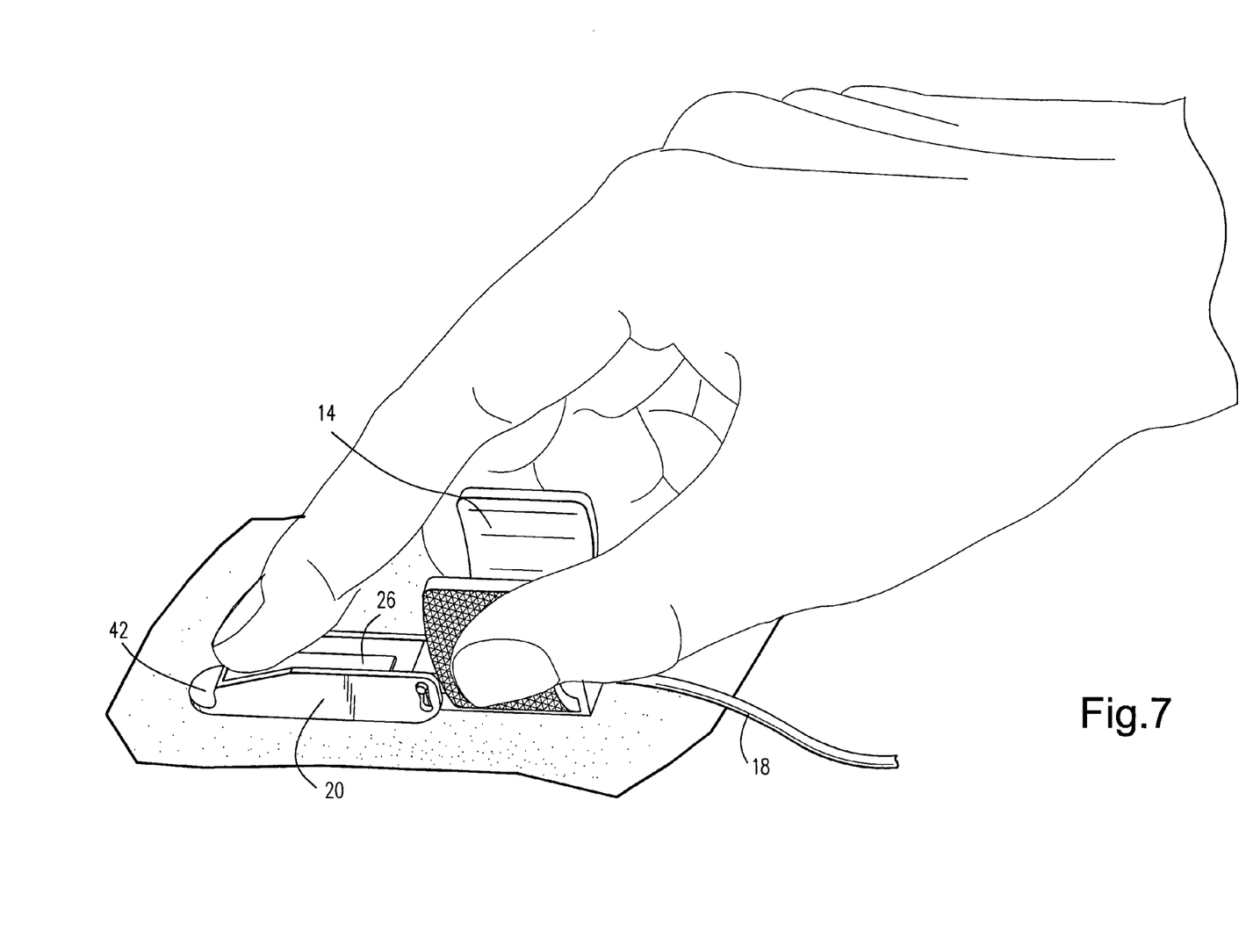
Figure 8:
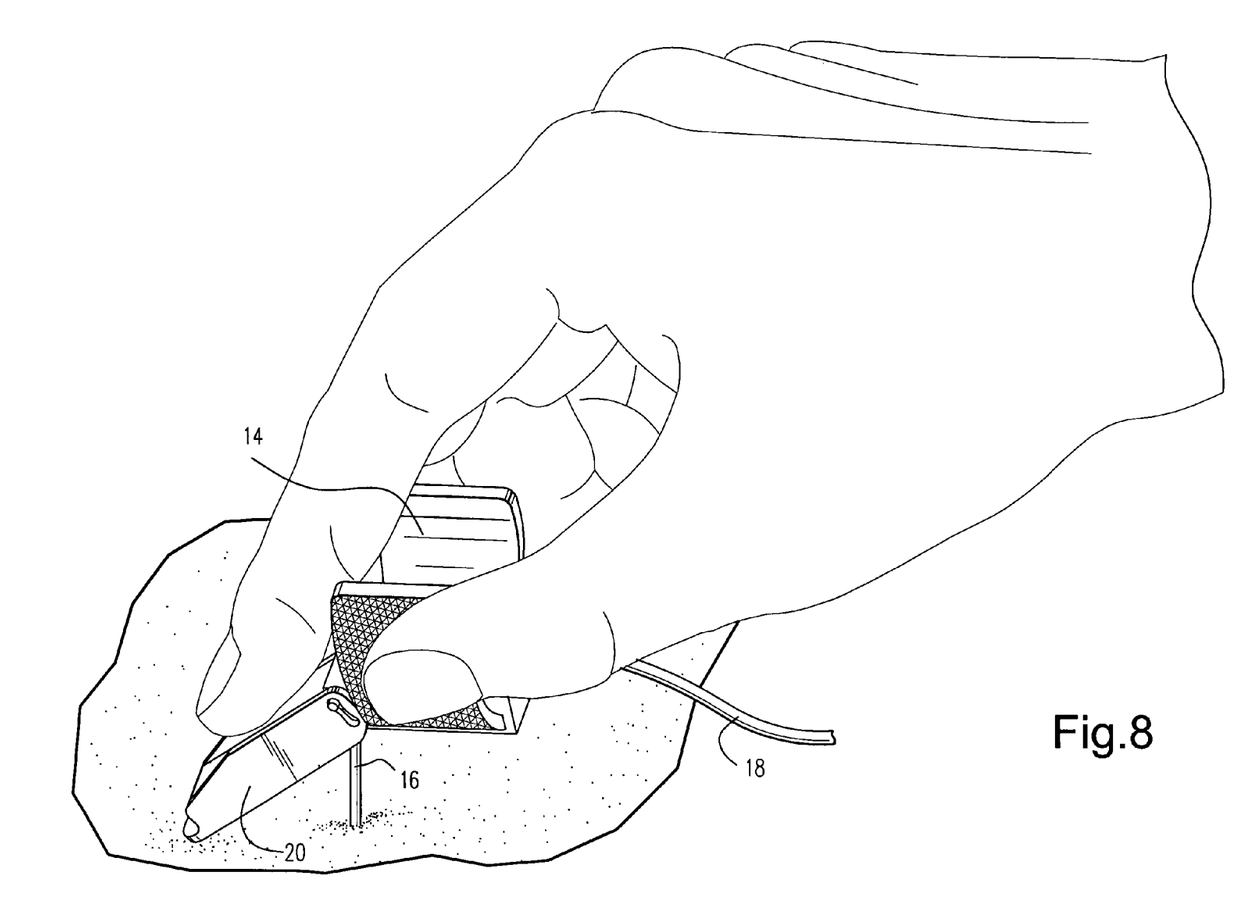

Upon completion of the infusion, the tape is removed while maintaining the infusion device in place at the injection site. The wings 14 are then grasped and flexed and the practitioner's index finger is applied to the guard as illustrated in FIG. 7. Upon withdrawal of the needle from the injection site, the guard is pivoted downwardly, as illustrated in FIG. 8, by the practitioner's index finger. The pivoting of the guard downwardly upon removal of the needle enables the needle to align with the slot 30. That is, the guard 20 is pivoted the approximately 90° of additional rotary movement to complete about 270° of rotation from its initial or first position overlying body 20 into its second position to encapsulate the needle. Because the entry to the slot 30 is offset from the pivot location of the guard, the needle will initially enter the proximal end of slot 30. Upon further pivotal movement of the guard toward the needle, i.e., toward the second and final position, and completing the full range of movement of the guard through about 270°, the needle will flex the one or more members 28 to progressively pass through slot 30 and enter the receptacle 22. Once needle 16 is received in the receptacle 22, as confirmed by an audible click, the one or more members will flex back to their normal position, maintaining the needle encapsulated within the guard. The audible click occurs as the guard 20 is fully pivoted into its second position and the members 28 flex past the needle to return to their normal unbiased condition. It will be appreciated that the guard 20 is also linearly displaced by moving the bosses 39 past pins 40 when the guard 20 is pivoted into its second position. Thus, the pins 40 reside in the opposite ends of slots 38 in the final needle encapsulating position of the guard. Once in that configuration, the infusion device may be disposed into a medical waste container, not shown, without danger of needlestick injury since the needle is totally captured by and encapsulated within the guard.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An infusion device comprising:
   an elongated body having a needle projecting from adjacent one end of said body and extending generally perpendicular to said body for transmitting fluid passing through the body into an injection site;
   a pair of flexible wings extending laterally from respective opposite sides of said body and lying in a plane generally perpendicular to said needle; and
   an elongated needle guard having a receptacle extending along one side thereof and coupled to said body adjacent said one end so as to enable both pivotal and sliding movement of said needle guard as said needle guard rotates through an arc of about 270° relative to said body, between a first position overlying said body and a second position receiving said needle within said receptacle.

2. An infusion device guard according to claim 1 wherein said guard includes a pair of elongated slots adjacent one end thereof and said body includes projections adjacent said one end of said body engaging in said slots enabling said pivotal and sliding movement of said guard relative to said body.

3. An infusion device according to claim 2 wherein said projections engage in respective ends of said slots when said guard lies in said first position and in opposite ends of said slots when said guard lies in said second position.

4. An infusion device according to claim 3 wherein said receptacle has an elongated entry slot formed by at least one elongated member, said guard being slidable relative to said projections and toward said opposite ends of said slots to orient the guard into a generally parallel relation to said needle upon movement of said guard into said second position.

5. An infusion device according to claim 3 wherein said one end of said guard includes a pair of projecting ears straddling said one end of said body, said slots in said ears extending in a direction generally parallel to the direction the needle extends from said body when said guard lies in said first position.

6. An infusion device according to claim 1 wherein said guard has an elongated entry slot for entry of the needle into the receptacle and formed in part by at least one elongated member.

7. An infusion device according to claim 6 wherein said entry slot is tapered inwardly toward the receptacle to facilitate entry of the needle into the slot and receptacle as the guard is pivoted toward said second position.

8. An infusion device according to claim 6 wherein said elongated member on said guard is resilient, enabling the needle to enter the slot by flexing the member and pass into the receptacle whereby the member precludes pivotal movement of the guard from the second position toward the first position.

9. An infusion device according to claim 1 wherein said guard has an elongated entry slot for entry of the needle into the receptacle and formed in part by at least one elongated member, said entry slot having a contour to facilitate entry of the needle into the slot and receptacle as the guard is pivoted toward said second position, said elongated member on said guard being resilient, enabling the needle to enter the slot by flexing the member to pass into the receptacle whereby the member precludes pivotal movement of the guard from the second position toward the first position.

10. An infusion device according to claim 9 wherein said member flexes back upon the needle passing into the receptacle to provide an audible indication that said guard lies in said second position encapsulating said needle.

11. An infusion device according to claim 1 wherein said guard includes a channel extending along a side thereof opposite said one side for receiving at least a portion of said body within said channel when said guard lies in said first position.

12. An infusion device comprising:
    an elongated body having a needle projecting from adjacent one end of said body and extending generally perpendicular to said body for transmitting fluid passing through the body into an injection site;
    a pair of flexible wings extending laterally from respective opposite sides of said body and lying generally in a plane perpendicular to said needle; and
    an elongated needle guard having a receptacle extending along one side thereof and coupled to said body, said guard being movable through an arc of about 270° relative to said body, between a first position overlying said body in generally parallel relation thereto and a second position receiving said needle within said receptacle, said guard including a channel extending along a side thereof opposite said one side for receiving at least a portion of said body within said channel when said guard lies in said first position, said guard in said second position extending generally perpendicular to said body and generally parallel to said needle.

13. An infusion device according to claim 12 wherein said receptacle has an entry slot formed by at least one elongated member.

14. An infusion device according to claim 13 wherein said entry slot has a contoured opening to facilitate entry of the needle into the slot and receptacle as the guard is pivoted toward said second position.

15. A method of using and safeguarding an infusion device having an elongated body with flexible wings, a needle extending generally at right angles thereto and a guard pivotally carried by said body adjacent one end thereof comprising the steps of:

(a) grasping the wings and inserting said needle into an injection site while the guard lies in a first position overlying the elongated body to one side of said needle and between the wings when grasped;

(b) pivoting the guard through about 180° to an intermediate position extended from and generally parallel to said body and on a an opposite side of the needle remote from the body during the infusion; and (c) upon completion of the infusion, grasping the wings and rotating the guard into a second position to encapsulate the needle.

16. A method according to claim 15 wherein step (c) includes linearly displacing the guard relative to the body into the second position to encapsulate the needle.

17. A method according to claim 16 wherein step (c) includes both linearly displacing and rotating the guard relative to the body into the second position to encapsulate the needle.

18. A method according to claim 15 including releasably securing the infusion device to a patient's skin.

19. A method according to claim 15 wherein step (c) includes pivoting the guard from said intermediate position through about 90° and into said second position.

20. A method according to claim 15 wherein steps (a) and (b) are carried out by pivoting the guard in the same rotational direction.

21. A method according to claim 15 wherein step (c) includes providing an audible indication that the guard has been rotated into said second position to encapsulate the needle.

22. An infusion device comprising:

an elongated body having a needle projecting from adjacent one end of said body and extending generally perpendicular to said body for transmitting fluid passing through the body into an injection site;

a pair of flexible wings extending laterally from respective opposite sides of said body and lying generally in a plane perpendicular to said needle;

an elongated needle guard having a receptacle extending along one side thereof and coupled to said body, said guard being movable through an arc of about 270° relative to the body between a first position overlying said body in generally parallel relation thereto and a second position receiving said needle within said receptacle, said guard in said second position extending generally perpendicular to said body and generally parallel to said needle; and said guard including a pair of elongated slots adjacent one end thereof and said body includes projections adjacent said one end of said body engaging in said slots enabling both pivotal and slidable movement of said slots and said projections relative to one another whereby said guard and said body both pivot and slide relative to one another as the guard approaches the said second position thereof enabling orientation of the guard into a generally parallel relation to the needle in the second position of said guard.

* * * * *